US008242262B2

(12) United States Patent
Dei et al.

(10) Patent No.: US 8,242,262 B2
(45) Date of Patent: Aug. 14, 2012

(54) PROCESS FOR PREPARING CHLORIDES OF PHTHALOCYANINE DERIVATIVES COMPRISING AT LEAST A QUATERNARY AMMONIUM GROUP

(75) Inventors: Donata Dei, San Gimignano (IT); Giacomo Chiti, Montemurlo (IT); Daniele Nistri, Prato (IT); Gabrio Roncucci, Colle Val d'Elsa (IT); Aldo Hendrikus Velders, Hengelo (NL); Salvatore Demartis, Sassari (IT); Valentina Paschetta, Ferrone (IT)

(73) Assignee: L. Molteni & C. Dei Fratelli Alitti Societa'di Esercizio S.p.A., Scandicci (IT)

( * ) Notice: Subject to any disclaimer, the term of this patent is extended or adjusted under 35 U.S.C. 154(b) by 1256 days.

(21) Appl. No.: 11/913,540

(22) PCT Filed: May 4, 2006

(86) PCT No.: PCT/EP2006/062059
§ 371 (c)(1),
(2), (4) Date: Nov. 2, 2007

(87) PCT Pub. No.: WO2006/117396
PCT Pub. Date: Nov. 9, 2006

(65) Prior Publication Data
US 2009/0131393 A1    May 21, 2009

(30) Foreign Application Priority Data

May 5, 2005  (IT) ............................... FI2005A0093

(51) Int. Cl.
*C07B 47/00*  (2006.01)
*C07D 487/22*  (2006.01)
(52) U.S. Cl. .................................................... 540/145
(58) Field of Classification Search .................. 540/145
See application file for complete search history.

(56) References Cited

U.S. PATENT DOCUMENTS

| 5,281,616 A | 1/1994 | Dixon et al. |
| 5,834,455 A | 11/1998 | Russell et al. |
| 5,965,598 A | 10/1999 | Roncucci et al. |
| 6,630,128 B1 | 10/2003 | Love et al. |
| 7,144,879 B2 | 12/2006 | Roncucci et al. |

FOREIGN PATENT DOCUMENTS

| EP | 186404 A2 | 7/1986 |
| EP | 906758 A1 | 4/1999 |
| EP | 1164135 A1 | 12/2001 |
| EP | 1356813 A1 | 10/2003 |
| EP | 1381611 B1 | 1/2004 |
| WO | WO 02/090361 A1 | 11/2002 |
| WO | WO 03/037902 A1 | 5/2003 |

OTHER PUBLICATIONS

Soncin et al., Photochemical & Photobiological Sciences (2002), 1(10), 815-819.*
Ben-Hur, E. and Rosenthal, I. 1985 "The phthalocyanines: a new class of mammalian cells photosensitizers with a potential for cancer phototherapy" *Int J Radiat Biol Relat Stud Phys Chem Med* 47:145-147.
Dummin, H. et al. (1997) "Selective photosensitization of mitochondria in hela cells by cationic zn(II) phthalocyanines with lipophilic side-chains" Journal of Photochemistry and Photobiology B: Biology 37:2319-229.
Fabris et al. 2005 "A novel tetracationic phthalocyanine as a potential skin phototherapeutic agent" *Experimental Dermatology* 14: 675-683.
Griffiths, J. (1997) "Some observations on the synthesis of polysubstituted zinc phthalocyanine sensitisers for photodynamic therapy" Dyes and Pigments 33:65-78.
Hongjian et al. (1996) "Studies of the supramolecular system of prophyrin-phthalocyanine formed by molecular self-assembly and its photoinduced electron transfer process" Acta Physico Chimica Sinica 12:44-48.
Mao et al. 1998 "Molecular deposition film of porphyrin and pthalocyanine bearing oppositely charged substituents" *Science in China* (Series B) 41:449-454.
Minnock, A. et al. (1996) "Photoinactivation of bacteria. Use of a cationic water-soluble zinc phthalocyanine to photoinactivate both gram-negative and gram-positive bacteria" Journal of Photochemistry and Photobiology B: Biology 32:159-164.
Wohrle, D. et al. (1990) "Synthesis of positively charged phthalocyanines and their activity in the photodynamic therapy of cancer cells" Photochemistry and Photobiology 51:351-356.

* cited by examiner

*Primary Examiner* — Paul V. Ward
(74) *Attorney, Agent, or Firm* — Knobbe Martens Olson & Bear LLP

(57) ABSTRACT

A process is described for preparing chlorides of phthalocyanine derivatives comprising at least a quaternary ammonium group, products useful as photosensitizing agents in photodynamic therapy.

34 Claims, No Drawings

PROCESS FOR PREPARING CHLORIDES OF PHTHALOCYANINE DERIVATIVES COMPRISING AT LEAST A QUATERNARY AMMONIUM GROUP

CROSS-REFERENCE TO RELATED APPLICATIONS

This application is the U.S. National Phase under 35 U.S.C. §371 of International Application No. PCT/EP2006/062059, filed May 4, 2006, which claims priority to Italian Patent Application No. FI2005A000093, filed May 5, 2005.

FIELD OF THE INVENTION

The invention relates to the field of organic synthesis, and in particular to a process for preparing chlorides of phthalocyanine derivatives comprising at least a quaternary ammonium group, having general formula (I) given hereinafter.

STATE OF THE ART

Molecules containing the phthalocyanine chromofluorophore macrocycle are known to produce reactive oxygen species, in particular radicals or singlet oxygen, by interacting with visible light.

Because of these properties, phthalocyanine compounds have long been used in photodynamic therapy (hereinafter referred to by the abbreviation "PDT") for both therapeutic treatment and diagnostic purposes.

Examples of said compounds are described by Ben-Hur E. et al. in *Int J Radiat. Biol.*, Vol. 47, pp. 145-147, 1985. Other photosensitising agents useful in PDT are the Zinc phthalocyanine complexes and their conjugates described in U.S. Pat. No. 5,965,598, in the name of the Applicant. These compounds have proven to be effective photosensitising agents in PDT treatment for both tumours and microbial infections because, after administration, they accumulate in tumour cells or in micro-organisms and, following irradiation with visible light, generate reactive oxygen species in sufficient quantities to damage the cells in which they are located.

As far as the Applicant's knowledge extends, processes for preparing substituted metal phthalocyanines described in the literature to date, such as the process described in U.S. Pat. No. 5,965,598 or European Patent No. 1 164 135 both in the name of the Applicant, are not suitable for preparing cationic phthalocyanine chlorides such as the present compounds of formula (I).

In EP No. 1 164 135 for example, a process was described for preparing cationic metal phthalocyanines by reacting the corresponding neutral compounds with an alkylating agent. This type of process has however proved only suitable for preparing cationic phthalocyanine iodides, whereas if the product of interest is the chloride, this synthetic path is not suitable for their preparation with acceptable yield and purity.

Given that the chlorides of cationic phthalocyanine derivatives appear to be particularly suitable as photosensitising agents due to their limited toxicity and also possess high solubility in water and excipients used for formulations, the need was strongly felt for an efficient process for preparing said derivatives with high purity.

SUMMARY OF THE INVENTION

The Applicant has now established a new process for preparing chlorides of phthalocyanine derivatives, comprising at least one quaternary ammonium group and having the general formula (I) given hereinafter, which enables final products of high purity to be efficiently obtained.

Therefore the present invention provides a process for preparing chlorides of phthalocyanine derivatives of formula (I)

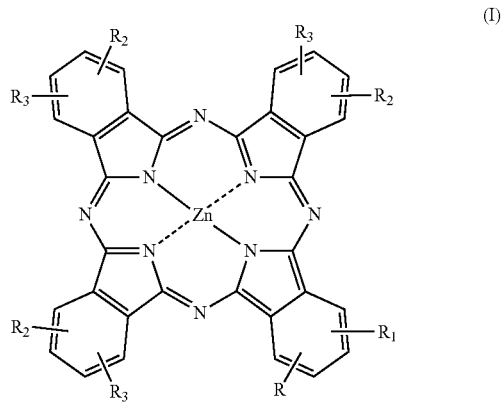

in which

R is chosen from H, groups containing at least one quaternary ammonium substituent, and groups suitable for conjugation to specific carriers, $R_1$, being the same as or different from $R_1$ is chosen from H and groups containing at least one quaternary ammonium substituent, $R_2$ and $R_3$, being the same or different, are chosen from H, groups chosen from alkoxy or thioalkoxy groups having from 1 to 10 carbon atoms, and groups containing at least one quaternary ammonium substituent, with the proviso that:

a) at least one amongst R, $R_1$, $R_2$ and $R_3$ is a group containing at least one quaternary ammonium substituent and, when R, $R_1$, $R_2$ and $R_3$ are groups containing at least one quaternary ammonium substituent, or R and $R_2$ are groups containing at least one quaternary ammonium substituent and $R_1$ and $R_3$ are H, said groups containing at least one quaternary ammonium substituent are the same;

b) when R and $R_1$ are both different from H, they are in positions 1,4 or 2,3, whereas when only one of R and $R_1$ is different from H, it is in position 1 or 2;

c) when $R_2$ and $R_3$ are both different from H, they are in positions 8, 11, 15, 18, 22, 25 or 9, 10, 16, 17, 23, 24 whereas when only one of $R_2$ and $R_3$ is different from H, it is in positions 8(11), 15(18), 22(25) or in positions 9(10), 16(17), 23(24); said process comprising the following steps:

i) reacting a phthalocyanine of formula (II) with a suitable alkylating agent to obtain the corresponding salt of the phthalocyanine of formula (I):

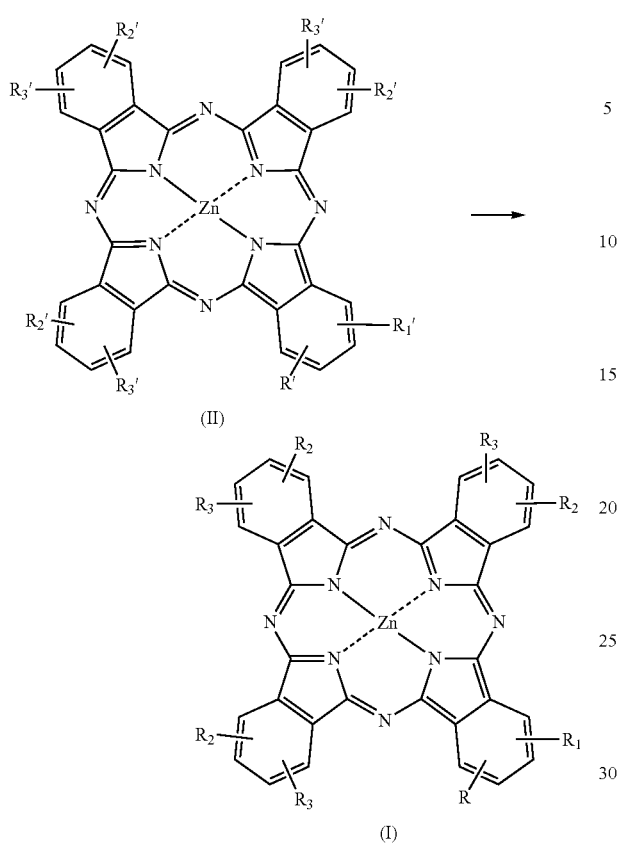

(II)

(I)

in which R, $R_1$, $R_2$ and $R_3$ are as defined above, while R', $R'_1$, $R'_2$, $R'_3$ are groups containing at least one amino substituent corresponding respectively to R, $R_1$, $R_2$, and $R_3$ when R, $R_1$, $R_2$ and $R_3$ are groups containing at least one quaternary ammonium substituent, while being the same as R, $R_1$, $R_2$, $R_3$ in all other cases, with the proviso that at least one of R', $R'_1$, $R'_2$ and $R'_3$ is a group containing at least one amino substituent and that the positions occupied by R', $R'_1$, $R'_2$, $R'_3$ are the same as specified above for R, $R_1$, $R_2$ and $R_3$;
ii) treating the ammonium salt of the phthalocyanine of formula (I) coming from step i) with a suitable ion exchange resin to obtain the corresponding phthalocyanine of formula (I) in chloride form.

A further subject of the invention are the aforesaid intermediates of formula (II), in which R'=$R_2$'=H and $R_1$'=$R_3$'=4-N,N-dimethylamino phenoxy or R'=$R_2$'=$R_1$'=$R_3$'=4-N,N-dimethylamino phenoxy and the iodides of said phthalocyanine derivatives of formula (I), in which R=$R_2$=H and $R_1$=$R_3$=4-N,N,N-trimethylammonium phenoxy, or R=$R_2$=$R_1$=$R_3$=4-N,N,N-trimethylammonium phenoxy, as process intermediates.

The characteristics and advantages of the invention will be illustrated in detail in the following description.

DETAILED DESCRIPTION OF THE INVENTION

The iodides of the phthalocyanine derivatives of formula (I) in which R=$R_2$=H and $R_1$=$R_3$=4-N,N,N-trimethylammonium phenoxy, or R=$R_2$=$R_1$=$R_3$=4-N,N,N-trimethylammonium phenoxy, and the corresponding compounds of formula (II) in which R'=$R_2$'=H and $R_1$'=$R_3'=_4$-N,N-dimethylamino phenoxy, or R'=$R_2$'=$R_1$'=$R_3$'=4-N,N-dimethylamino phenoxy, which form as intermediates in the process of the invention, are new products never previously described.

The process of the invention has been provided by the Applicant for preparing the aforesaid chlorides of the phthalocyanine derivatives of formula (I), in particular the derivatives of formula (I) and the corresponding intermediates of formula (II) in which:
R=R'=$R_2$=$R_2$'=H, $R_1$=$R_3$=group containing at least one quaternary ammonium group and $R_1$'=$R_3$'=group containing at least one amino group corresponding to said quaternary ammonium; or
R=$R_1$=$R_2$=$R_3$=group containing at least one quaternary ammonium group and R'=$R_1$'=$R_2$'=$R_3$'=group containing at least one amino group corresponding to said quaternary ammonium; or
R=group containing at least one quaternary ammonium group, R'=group containing at least one amino group corresponding to said quaternary ammonium, $R_1$=$R_1$'=H or $R_1$=R and $R_1$'=R', and $R_2$=$R_2$'=$R_3$=$R_3$'=H; or
R=R'=group suitable for conjugation to specific carriers, $R_1$=$R_1$'=H, $R_2$=group containing at least one quaternary ammonium group, $R_2$'=group containing at least one amino group corresponding to said quaternary ammonium, $R_3$=$R_2$, H and $R_3$'=$R_2$', H.

In the case of tetrasubstituted phthalocyanine derivatives, the process of the invention can be carried out either on isomeric mixtures or on a single isomer, they being obtained for example from the starting isomeric mixture by using the separation process described in International patent application No. WO 03/037902 in the name of the Applicant.

Within the scope of the present invention, the expression "groups containing at least one quaternary ammonium substituent" means for example a $(X)_p R_4$, where X is chosen from the group consisting of O, —$CH_2$—, CO, S, SO, and —$NR_5$ where $R_5$ is chosen from H and C1-C15 alkyl; and $R_4$ is

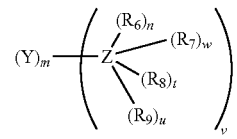

in which
Y is selected from the group consisting of C1-10 alkyl and phenyl, possibly substituted, or forms with the Z group, to which it is bound, a saturated or unsaturated heterocycle, possibly substituted, which may contain up to two heteroatoms selected from the group consisting of N, O and S;
Z is selected from the group consisting of N, —$CH_2$N and —$CONHCH_2CH_2N$;
$R_6$ and $R_7$, equal or different from one another, are selected from the group consisting of C1-15 alkyl and phenyl or form with the Z group, to which they are bound, a saturated or unsaturated heterocycle, possibly substituted, which may contain up to two heteroatoms selected from the group consisting of N, O and S;
$R_8$ and $R_9$, equal or different from one another, are selected from the group consisting of H and C1-15 alkyl;
m, n, p, w, t and u, independently from one another, are 0 or 1; and
v is an integer comprised between 1 and 3,
with the proviso that only one from n, w, t and u is simultaneously 0, while the expression "corresponding group containing at least one amino substituent" means for example the corresponding $(X)_pR_4$ group defined as above in which two of n, w, t and u are simultaneously 0.

Of the groups containing at least one quaternary ammonium substituent, groups chosen from the following are preferred:

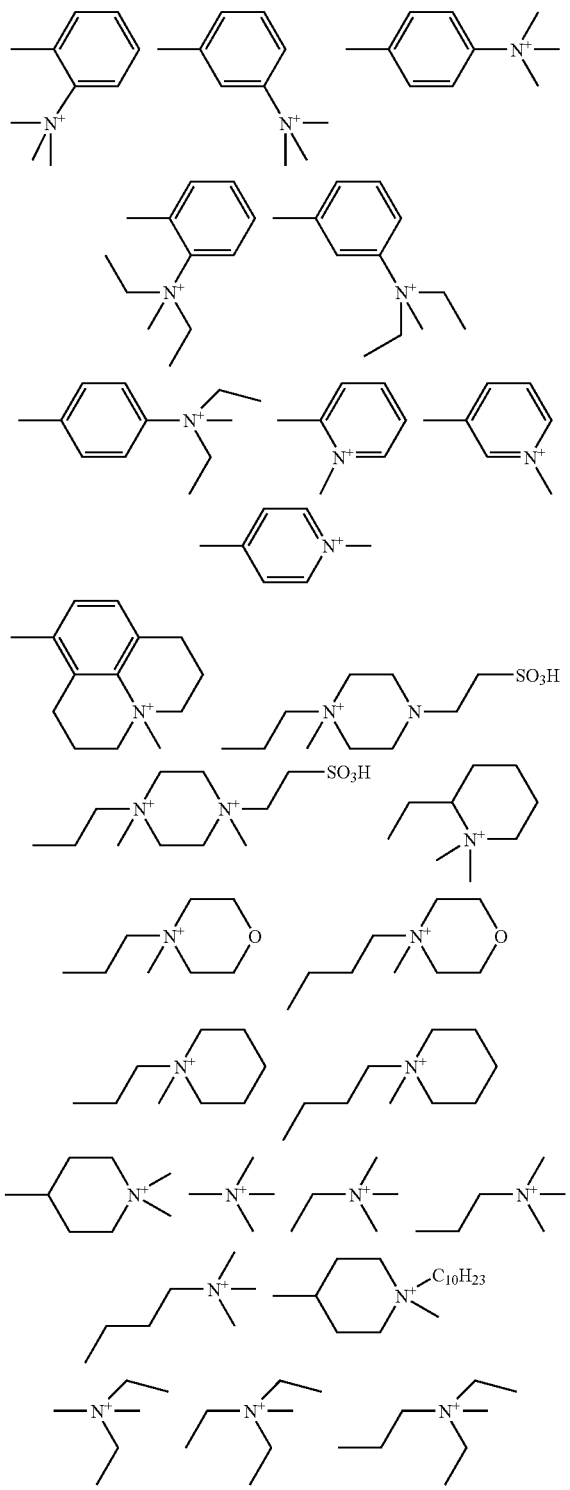
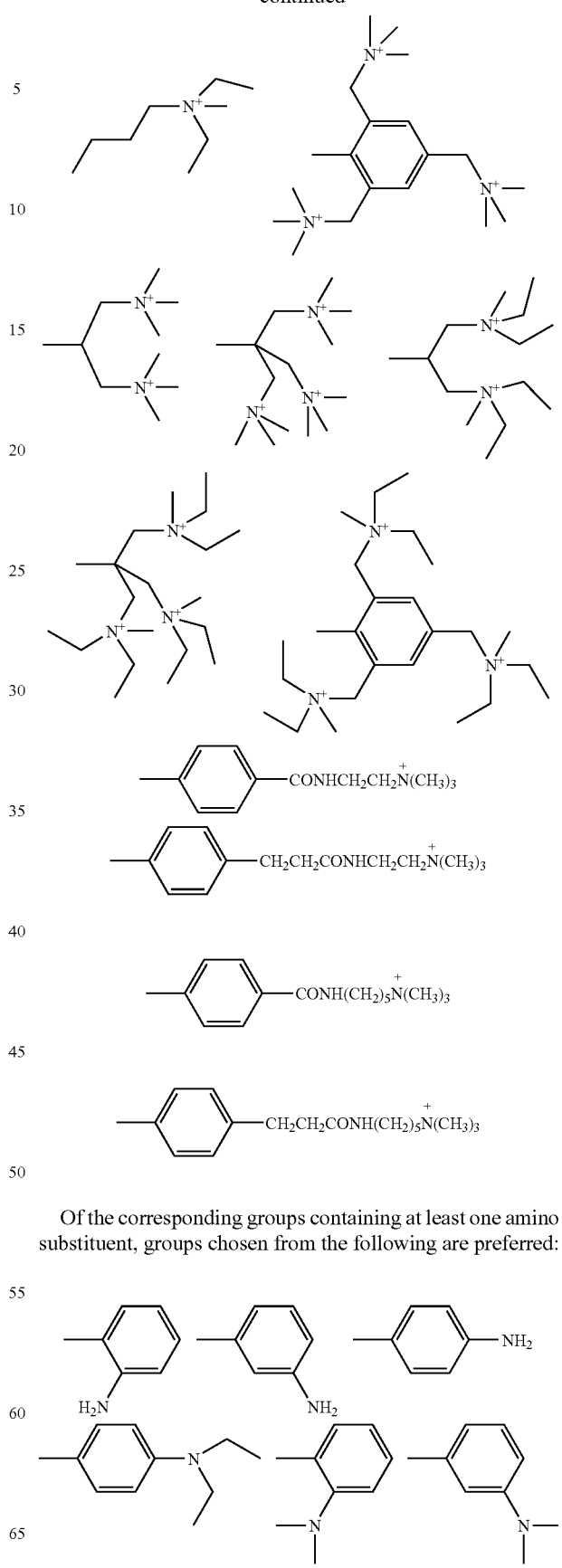

Of the corresponding groups containing at least one amino substituent, groups chosen from the following are preferred:

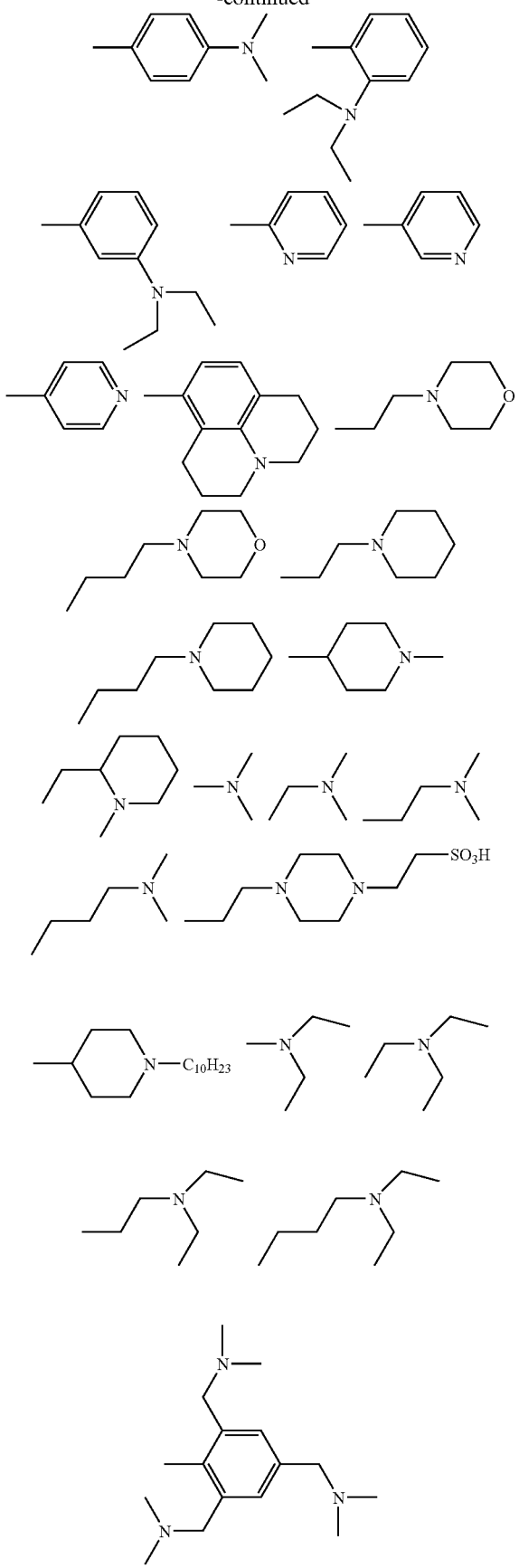
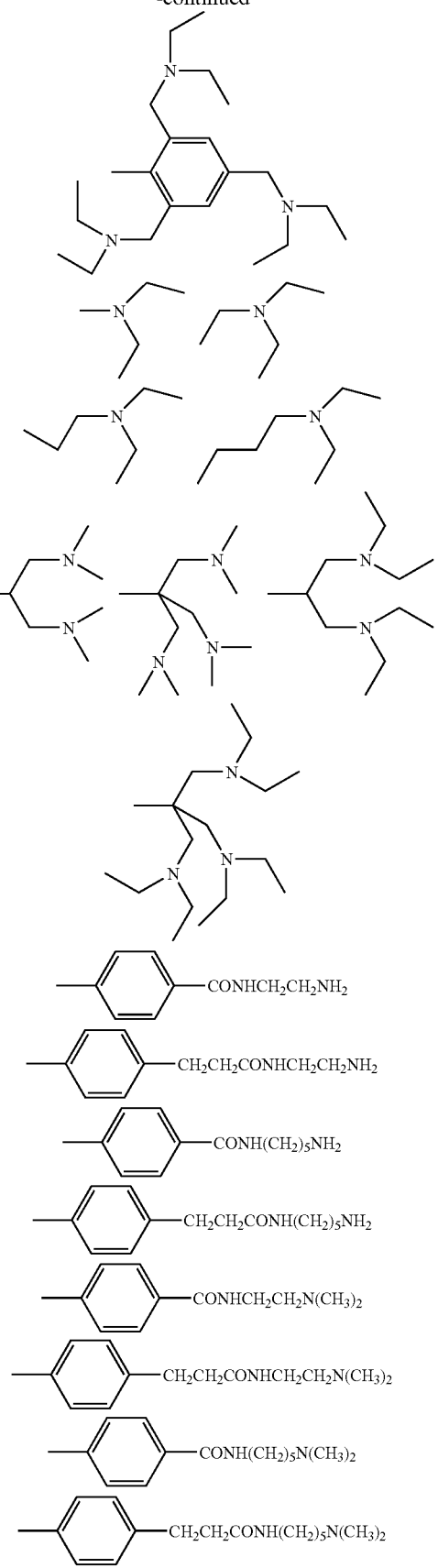

Particularly preferred are the following groups containing at least one ammonium substituent:

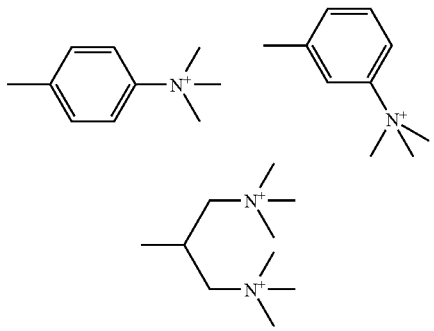

and the corresponding groups with amino substituents:

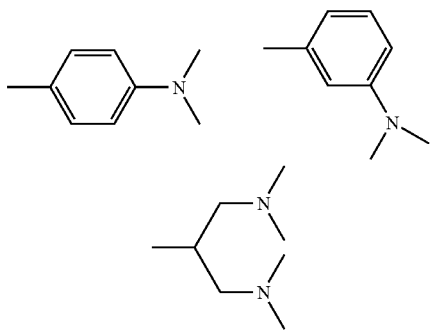

The term "saturated or unsaturated" heterocycle means preferably a heterocycle selected from the group consisting of morpholine, piperidine, pyridine, pyrimidine, piperazine, pyrrolidine, pyrroline, imidazole, aniline and julolidine.

The term "group suitable for conjugation to specific carriers" means any group suitable for binding, by means of covalent bonds, bio-organic carriers such as amino acids, polypeptides, proteins, antibodies, polysaccharides and aptamers, able to facilitate transport of the phthalocyanine to very precise targets: and preferably means a group selected from the group consisting of —COOH, —SH, —OH, —NH$_2$, —CO—CH$_2$—Br, —SO$_2$Cl, maleimide, hydrazide, phenol, imido, biotin, possibly bound to the phthalocyanine nucleus through a suitable spacer (X)$_p$—W, where X and p are defined as above and W is chosen from C1-C10 alkyl, aryl, and C1-C5 arylalkyl.

When R is a group suitable for conjugation to specific carriers, as defined above, preferably R$_1$=H and R$_2$ and R$_3$ are chosen from H and groups containing at least one quaternary ammonium substituent, provided that at least one of R$_2$ and R$_3$ is different from H.

The phthalocyanine derivatives of formula (II) that comprise the starting products of the present process can be prepared from commercial products with known procedures, already described for example in U.S. Pat. No. 5,965,598, in European Patent No. 1 164 135 and in European Patent No. 1 381 611, all in the name of the Applicant.

One of the known processes describes for example the base-catalysed condensation of suitably substituted phthalonitriles, in suitable ratios according to the final product required. This process was optimised by the Applicant to obtain the compounds of formula (II) which constitute the precursor intermediates of the ammonium salts of formula (I), by using as starting products the following two dinitriles of formula (III) and (IV)

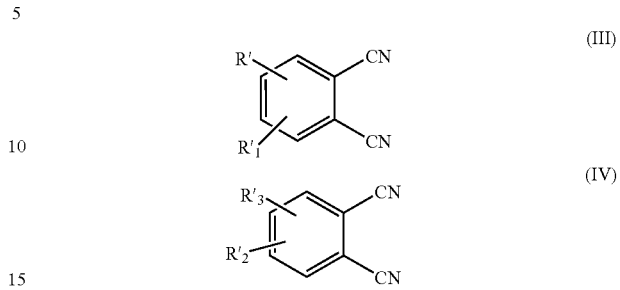

where R', R'$_1$, R'$_2$, R'$_3$ are as defined above.

As extensively described in the literature, to obtain centrosymmetrical phthalocyanines (i.e. compounds in which R'=R$_2$' and R$_1$'=R$_3$') the condensation is undertaken with a single phthalonitrile of formula (III), while to obtain non centrosymmetrical derivatives the phthalonitriles of formula (III) and (IV) are used in a (III):(IV) molar ratio between 1:1 and 1:10, preferably equal to 1:3.

The compounds of formula (III) and (IV) can in turn be obtained from commercial products by subjecting them to different reactions depending on the substitution required, but in any case using procedures commonly used and known to any expert of the art.

The condensation reaction between the dinitriles of formula (III) and (IV) is carried out in the presence of a base, in the presence or absence of a solvent and subjecting the reaction mixture to heating. In a subsequent step, or preferably simultaneously with the condensation, the central metal is inserted by adding a suitable Zinc(II) salt, preferably Zinc(II) acetate or Zinc(II) chloride.

The preferably used bases are strong organic non-nucleophilic bases such as 1,5-diazabicyclo[5.4.0]non-5-ene (DBN), 1,8-diazabicyclo[5.4.0]undec-7-ene (DBU) and 2-dimethylamino-ethanol (DMAE), but metal alcoholates or hydroxides can also be used.

The solvents are instead preferably chosen from high boiling and water miscible organic solvents, such as dimethylformamide (DMF).

The reaction can be carried out either in the presence or absence of solvent, in this case using the base also as a solubilizing agent; for preparing non centrosymmetrical phthalocyanine, use of solvent is preferable.

Reaction times range as a function of the scale of synthesis, while the reaction temperatures may range from 100 to 250° C., preferably between 130 and 180° C. Optimal results for preparing centrosymmetrical phthalocyanines are obtained when the condensation and simultaneous metal insertion reaction is carried out in the absence of solvent or in dimethylformamide using DBU as base in a quantity comprised between 1 and 10 equivalents, and adding Zinc(II) acetate in a quantity comprised between 0.25 and 2 equivalents with respect to the phthalonitrile of formula (III), at a temperature between 130 and 140° C.

The crude metal phthalocyanine is then obtained by treating the reaction mixture with water or mixtures of water and water miscible solvents, filtering or centrifuging the suspension and washing the recovered solid several times with water and/or water miscible solvents, preferably alcohols.

The crude product can be purified by column chromatography followed by re-precipitation from the solvent, prior to undergoing the subsequent step. For the chromatography, the stationary phase is for example a silica gel or alumina, while the mobile phase is a mixture of organic solvents, preferably composed of two or more solvents chosen from chlorinated solvents, THF, methanol, ethyl ether, n-hexane and DMF, where a high percentage of chloride solvents or THF is always present.

For the re-precipitation of phthalocyanine with 4 or 8 substituents, dichloromethane may for example be used as the solvent and n-hexane as the precipitant, while for mono- or di-substituted derivatives, mixtures of DMF are preferred with precipitants such as ethyl ether, either alone or mixed with other ethers.

The term "suitable alkylating agent" in step i) of the present process means for example an alkyl bromide, iodide or sulfate, being preferably a C1-C5 linear alkyl iodide. According to a particularly preferred embodiment of the invention the aforesaid alkylating agent is methyl iodide, used typically in a quantity between 1 and 20 equivalents per amino group to be methylated, preferably in a quantity comprised between 5 and 11 equivalents.

Moreover, the alkylating reaction is typically undertaken in a solvent, preferably selected from the group consisting of DMF, dimethylsulfoxide (hereinafter abbreviated to DMSO) and N-methylpyrrolidone (hereinafter abbreviated to NMP). Preferred is the process whereby alkylation step i) is carried out using a quantity of methyl iodide between 5 and 11 equivalents per amino group, and NMP as the solvent.

The reaction process comprises a fundamental step in the synthetic process, in that, if undertaken as described hereinafter, it guarantees an adequate removal of both the impurities and residual solvents from the intermediate quaternary ammonium salt and therefore a purity higher than 98% of the final chloride. Specifically, the reaction mixture must be diluted with a suitable solvent, preferably an alcohol, and the solution thus obtained treated with a precipitating solvent, preferably chosen from ethers.

In accordance with a particularly preferred embodiment of the present process, the ammonium salt of formula (I) not in chloride form is precipitated from the solution in NMP with ethyl ether or isopropyl ether in a quantity of 4-8 volumes relative to the volume of NMP, after having diluted the solution in NMP with methanol in a quantity of 1-2 volumes relative to the volume of NMP.

Where R' specifically contains an additional alkylable group in addition to the group or groups destined to be alkylated, by treating with the alkylating agent provided in step i) of the present process, protection of the functional group prior to alkylation at step i) and subsequent deprotection thereof is preferred. Said possible protection and deprotection reactions are carried out in accordance with procedures commonly used in organic synthesis and known to any expert in the art.

The ammonium salt intermediate of formula (I) is then transformed into a chloride by treating the product in solution with a suitable resin.

Ion exchange resins suitable for undertaking the present process are strong basic resins with quaternary ammonium functional groups, for example a polystyrene based resin with a degree of cross-linking between 4 and 10% such as Amberlite® IRA-400 (Cl) resin.

The exchange of ammonium salt for chloride at step ii) of the present process is preferably undertaken by chromatography of the aforesaid ammonium salt solution through the resin and recovering the product from the solution by evaporation, lyophilisation or precipitation.

In accordance with a preferred condition, the salt to be exchanged is dissolved in an alcoholic solvent, preferably methanol, or in a mixture of said alcoholic solvent with water or other solvents; if a mixture is used, the alcoholic solvent preferably comprises at least 70% of the mixture.

In accordance with a preferred embodiment of the process of the invention, step ii) is carried out by chromatography of a solution of the ammonium salt, different from the chloride, of the phthalocyanine of formula (I) in methanol through a suitable resin, then treating the eluate with ethyl ether to precipitate the required chloride of phthalocyanine (I).

According to a further preferred embodiment of the process of the invention, when the ion exchange resin is used, step ii) is carried out by chromatography by using a suitable resin and the phthalocyanine (I) iodide solution in a mixture of methanol and a solvent with high solubilizing power such as DMSO or DMF, preferably so that the co-solvent constitutes 1 to 20% by volume on the total volume of the methanol/co-solvent mixture, and re-precipitating from the eluate the obtained corresponding chloride by treatment with ethyl ether.

A preferred aspect of the process is the use of an eluent based on methanol or an aqueous mixture of water miscible solvents, rather than being exclusively aqueous, for the ion exchange chromatography in step ii). In this respect, with the aforedescribed process, the final chloride is found to be further purified from related compounds present, achieving a HPLC purity higher than 98%.

The following non-limiting examples of the present invention are given by way of illustration.

EXAMPLE 1 a) Synthesis of 3-(4-N,N-dimethylamino-phenoxy)phthalonitrile

To a solution of 3-nitrophthalonitrile (140 g, 0.81 mol) in dry DMSO (2 l), 3-(dimethylamino)phenol (165 g, 1.2 mol) and dry $K_2CO_3$ (370 g, 2.68 mol) were added and the suspension stirred and warmed at 40° C. for 2 h. After cooling to room temperature, the reaction mixture was poured in water (5 l) and, after 1 h of stirring, the obtained suspension was filtered. The solid was dissolved in $CH_2Cl_2$ (650 ml) and washed with NaOH 0.5M (650 ml). The organic phase was treated with charcoal and $Na_2SO_4$, filtered and the solvent eliminated at reduced pressure. The residue was finally treated with diisopropyl ether (550 ml) at 35° C. for half an hour, then cooled at 4° C. for 48 h and filtered to give 204 g of 3-(4-N,N-dimethylamino-phenoxy)phthalonitrile as a yellow solid (yield: 96%).

$^1$H-NMR (200 MHz, DMSO-$d_6$) δ, ppm 7.83-7.80 (m, 2H), 7.33-7.21 (m, 2H), 6.67 (dd, J=8.3 Hz, J=2.3 Hz, 1H), 6.57-6.54 (m, 1H), 6.43 (dd, J=7.9 Hz, J=2.0 Hz, 1H), 2.93 (s, 6H).

$^{13}$C-NMR (75 MHz, DMSO-$d_6$) δ, ppm 161.12, 155.53, 152.95, 136.57, 131.31, 128.39, 122.22, 116.38, 116.35, 114.19, 110.39, 107.43, 105.10, 104.35, 40.59. EI-MS m/z 263 [M$^+$].

b) Synthesis of Zinc (II) [1,8(11),15(18),22(25)-tetrakis-(4-N,N-dimethylamino phenoxy]phthalocyaninate Under nitrogen atmosphere 80 g of 3-(4-N,N-dimethylamino-phenoxy)phthalonitrile (0.3 mol), obtained as described above in point a), are dissolved in 460 ml of DBU (3 mol).

28 g of $Zn(AcO)_2$ (0.15 mol) are added to the solution thus obtained, then the reaction mixture is brought to 140° C. and maintained at this temperature, shielded from light, under nitrogen atmosphere and under vigorous stirring for 22 hours. After this time, the mixture is brought again to room temperature, then treated with 14 l of deionised $H_2O$; the suspension is filtered and the solid washed with $H_2O$ (2×2 l) and MeOH (1×1 l). The product thus obtained is purified by silica gel chromatography (mobile phase: $CH_2Cl_2$/MeOH from 98/2 to 95/5) followed by re-precipitation from the solvent, achieved by dissolving the product derived from the chromatography in 0.5 l of $CH_2Cl_2$ and re-precipitating it by adding 4 l of n-hexane. After filtering, washing with n-hexane (2×1 l) and drying, 60.1 g of product are obtained found to be the title product (yield=72.3%). The product was characterised by $^1H$-NMR analysis and mass spectrometry.

$^1H$-NMR (300 MHz, DMSO-$d_6$): δ=9.20-8.75 (m, 4H), 8.19-7.96 (m=4H), 7.59-6.70 (m, 20H), 2.93-2.90 (m, 24H) ppm.

ESI-MS: m/z 1117 [(M+H)$^+$].

c) Synthesis of Zinc(II) [1, 8(11),15(18),22(25)-tetrakis-(4-N,N,N-trimethylammonium phenoxy)]phthalocyaninate Tetrachloride 60 g of Zinc(II) [1,8(11),15(18),22(25)-tetrakis-(4-N,N-dimethylamino phenoxy)]phthalocyaninate (0.054 mol) obtained as aforedescribed in point b) are dissolved in 1.5 l of N-methylpyrrolidone (NMP).

150 ml of methyl iodide (2.4 mol) are then added and the solution maintained at room temperature, shielded from light, under nitrogen atmosphere and under vigorous stirring for 72 hours.

The reaction mixture thus obtained is diluted with 3 l of MeOH then treated with 12 l of isopropyl ether. The suspension so obtained is left under stirring for ½ hour, allowed to stand for 1 hour, then filtered and the solid washed with isopropyl ether (2×2 l) and ethyl ether (2×2 l).

94.7 g of wet product are thus obtained, used as such for the next step after sub-dividing them into two sub-batches.

This product, found to be Zinc(II) [1,8(11),15(18),22(25)-tetrakis-(4-N,N,N-trimethylammonium phenoxy)]phthalocyaninate tetraiodide, was characterised by $^1H$-NMR.

$^1H$-NMR (300 MHz, DMSO-$d_6$): δ=9.49-7.31 (m, 28H), 3.67-3.55 (m, 36H) ppm.

The 2 sub-batches of Zinc(II) [1,8(11),15(18),22(25)-tetrakis-(4-N,N,N-trimethylammonium phenoxy)]phthalocyaninate tetraiodide obtained as aforedescribed, each equal to 47.2 g, are processed as follows.

47.2 g of the aforesaid product are dissolved in 2 l of 4/1 MeOH/DMSO. The solution is subjected to column chromatography, whose stationary phase is prepared with 470 g of Amberlite® IRA 400 (Cl) resin, previously washed with an aqueous solution made acid with 0.5 M HCl and conditioned with 4/1 MeOH/DMSO. 12 l of ethyl ether are slowly added to the eluate, maintained under stirring. The suspension obtained is left to stand for 1 hour, then filtered and the solid washed with ethyl ether (4×0.5 l).

From the two procedures, 31.1 g and 32.1 g of wet product are obtained which are combined and re-precipitated by dissolving in 3 l of MeOH, and slowly adding 12 l of ethyl ether to the solution obtained, while maintaining under stirring. The suspension is left to stand for 1 hour, then filtered and the solid washed with ethyl ether (4×0.5 l).

After drying, 57.8 g of product are obtained, characterised as follows.

$^1H$-NMR (300 MHz, DMSO-$d_6$): δ=9.46-7.29 (m, 28H), 3.70-3.57 (m=36H) ppm. $^{13}C$-NMR (75 MHz, DMSO-$d_6$): δ=160.36 160.23 158.78 158.64 158.51 158.26 153.90 153.29 153.12 152.7 152.43 152.19 151.60 150.03 149.65 143.33 143.08 142.90 141.90 141.67 132.12 131.66 131.26 129.25 129.05 128.48 128.19 123.76 123.16 121.37 120.85 120.48 118.88 117.59 117.31 57.24 57.09 ppm. UV-vis (MeOH/$H_2O$ 50/50) $\lambda_{max}$ (%): 690 (100), 622 (18), 340(23).

ESI-MS: m/z 294, 1 [(M-4Cl)$^{4+}$].

EXAMPLE 2

Synthesis of Zinc(II) [2,9(10),16(17),23(24)-tetrakis-(4-N,N,N-trimethylammonium phenoxy)]phthalocyaninate Tetrachloride By following the procedure described in Example 1 above and using 4-nitrophthalonitrile in place of 3-nitrophthalonitrile, the title compound was prepared.

EXAMPLE 3

Synthesis of Zinc(II) [2,3,9,10,16,17,23,24-octakis-(4-N,N,N-trimethylammonium phenoxy)]phthalocyaninate Octachloride By following the procedure described in Example 1 above and using 4,5-dichlorophthalonitrile in place of 3-nitrophthalonitrile, the title compound was prepared.

EXAMPLE 4 a) Synthesis of Zinc(II) [1,8(11),15(18),22(25)-tetrakis-(3-N,N-dimethylamino phenoxy)]phthalocyaninate 55 g of 3-(3-N,N-dimethylamino phenoxy) phthalonitrile (0.21 mol) are dissolved in 300 ml of DMF under nitrogen atmosphere. 18.3 g of Zn(AcO)$_2$ (0.11 mol) and 150 ml of DBU (1 mol) are added and the reaction mixture is brought to 130° C., maintained at this temperature, shielded from light, under nitrogen atmosphere and under vigorous stirring for 12 hours. The reaction mixture is then brought to 0° C., treated with 1.8 l of deionised $H_2O$ and maintained under stirring at 0° C. for half an hour, then the suspension is filtered and the solid washed with $H_2O$ in portions (1.3 l in total) and MeOH (1×750 ml+1×180 ml).

The product is then subjected to chromatographic purification on silica gel (mobile phase: 50/1 $CH_2Cl_2$/DMF) followed by treating the purified solid with ethyl ether (200 ml) for 1 hour, filtering, then washing the solid with ethyl ether (2×25 ml). The product thus purified is dissolved in 0.5 l of $CH_2Cl_2$ and re-precipitated by adding 4 l n-hexane. After filtering, washing with n-hexane (2×1 l) and drying, 60.1 g of product are obtained.

$^1H$-NMR (300 MHz, DMSO-$d_6$): δ=9.30-8.68 (m, 4H), 8.22-7.89 (m=4H), 7.77-7.37 (m=4H), 7.20-6.40 (m, 16H), 3.02-2.79 (m=24H) ppm.

FAB-MS: m/z 1117 [(M+H)$^+$].

b) Synthesis of Zinc(II) [1,8(11), 15(18),22(25)-tetrakis-(3-N,N,N-trimethylammonium phenoxy)]phthalocyaninate Tetrachloride 34 g (0.03 mol) of Zinc(II) [1,8(11),15(18),22(25)-tetrakis-(3-N,N-dimethylamino phenoxy)]phthalocyaninate obtained as aforedescribed in point a) are dissolved in 850 ml of NMP, then 85 ml (1.4 mol) of MeI are added and the solution is maintained at this temperature, shielded from light, under nitrogen atmosphere and under vigorous stirring for 96 hours.

The reaction mixture is diluted with 1.7 l of MeOH, then treated with 6.8 l of ethyl ether, obtaining a suspension which is left under stirring for half an hour, allowed to stand for 1 hour then filtered; the recovered solid is washed with ethyl ether (2×0.5 l) to obtain 60 g of wet product, found to be Zinc(II) [1,8(11),15(18),22(25)-tetrakis-(3-N,N,N-trimethylammonium phenoxy)]phthalocyaninate tetraiodide characterised by mass spectrometry and $^1$H-NMR.

$^1$H-NMR (300 MHz, DMSO-$d_6$): δ=9.49-7.19 (m, 28H), 3.67-3.53 (m=36H) ppm. ESI-MS: m/z 294.1 [(M-4I)$^{4+}$].

60 g of this product were dissolved in 5.5 l of MeOH and the solution passed through a chromatography column having 500 g of Amberlite® IRA 400 (Cl) resin as the stationary phase, previously washed with an aqueous solution made acid with 0.5 M HCl and conditioned with MeOH. Ethyl ether (24 l) is slowly added to the eluate (about 6 l), maintaining under stirring. The suspension obtained is allowed to stand for 1 hour then filtered. The recovered solid is washed with ethyl ether (2×250 ml) and dried on a filter for about an hour. 36 g of the title product are obtained.

$^1$H-NMR (300 MHz, DMSO-$d_6$): δ=9.45-7.23 (m, 28H), 3.77-3.58 (m=36H) ppm. UV-vis (MeOH/H$_2$O 50/50) $\lambda_{max}$ (%): 698 (100), 628(18), 346(21).

ESI-MS: m/z 294.1 [(M-4Cl)$^{4+}$].

EXAMPLE 5 a) Synthesis of Zinc(II) 2-{2-(dimethylamino)-1-[(dimethylamino) methyl]ethoxy}phthalocyaninate Under nitrogen atmosphere 48 g of 4-{2-(dimethylamino)-1-[(dimethylamino)methyl]ethoxy}phthalonitrile (0.18 mol) and 68 g of 1,2-dicyanobenzene (0.53 mol) are dissolved in 420 ml of DMF.

32.4 g of Zn(AcO)$_2$ (0.18 mol) and 136 ml of DBU (0.90 mol) are added and the reaction mixture is brought to 130° C. and maintained at this temperature, shielded from light, under nitrogen atmosphere and under vigorous stirring for 20 hours.

The reaction mixture is then cooled to about 50° C. and treated with 800 ml of deionised H$_2$O; the suspension thus obtained is filtered and the recovered solid is washed with H$_2$O in portions (2×400 ml) then with 8/2 acetone/ethyl ether (2×500 ml).

The product is subjected to chromatographic purification on silica gel (mobile phase: THF/DMF 9/1), followed by re-precipitation from DMF (400 ml)/Et$_2$O (1.6 l)/n-hexane (12 l) to obtain 35.6 g of product (yield=27%).

$^1$H-NMR (300 MHz, DMSO-$d_6$): δ=9.28-9.25 (m, 6H), 9.14 (d, 1H, J=8.4 Hz), 8.87 (s, 1H), 8.21-8.19 (m, 6H), 7.79 (d, 1H, J=8.4 Hz), 5.17 (t, 1H, J=5 Hz) 2.86 (d, 4H, J=5 Hz), 2.5 (s, 12H) ppm.

ESI-MS: m/z 721 [(M+H)$^+$].

b) Synthesis of Zinc(II) 2-{2-(trimethylammonium)-1-[(trimethylammonium)methyl]ethoxy}phthalocyaninate Dichloride 30.2 g (0.042 mol) of Zinc(II) 2-{2-(dimethylamino)-1-[(dimethylamino)methyl]ethoxy}phthalocyaninate obtained as aforedescribed in point a) are dissolved in 900 ml of NMP. 60 ml of MeI (1 mol) are added and the solution maintained under room temperature, shielded from light, under nitrogen atmosphere and under vigorous stirring for 72 hours. The reaction mixture is diluted with 1.4 l of MeOH, then treated with 5.5 l of ethyl ether. The suspension thus obtained is then left under stirring for half an hour, allowed to stand for 1 hour then filtered. The recovered solid is washed with ethyl ether (4×0.5 l) to finally obtain 47 g of wet product, found to be Zinc(II) 2-{2-(trimethylammonium)[(trimethylammonium) methyl]ethoxy}phthalocyaninate diiodide.

$^1$H-NMR (300 MHz, DMSO-$d_6$): δ=9.46-9.43 (m, 7H), 9.19 (bs=1H), 8.29-8.27 (m, 6H), 8.17 (d, 1H, J=10 Hz), 6.20-6.10 (m, 1H), 4.22-4.04 (m=4H), 3.41 (s, 18H) ppm.

10.1 g of this product are dissolved in 250 ml of a 4/1 MeOH/DMF mixture. The solution is passed through a chromatography column having 500 g of Amberlite® IRA 400 (Cl) resin as the stationary phase, previously washed with an aqueous solution made acid with 0.5 M HCl and conditioned with 4/1 MeOH/DMF. Ethyl ether (2 l) is slowly added to the eluate (about 500 ml) while maintaining under stirring, and the suspension obtained is allowed to rest for 1 hour at 4° C. then filtered; the recovered solid is washed with ethyl ether (4×500 ml) to obtain, after drying, 6.9 g of the title product.

$^1$H-NMR (300 MHz, DMSO-$d_6$): δ=9.43-9.40 (m, 7H), 9.19 (bs=1H), 8.26-8.22 (m, 6H), 8.17 (d, 1H, J=10 Hz), 6.20-6.18 (m, 1H), 4.19-4.17 (m=4H), 3.42 (s, 18H) ppm.

$^{13}$C-NMR (75 MHz, DMSO-$d_6$): δ=156.20, 154.40, 154.17, 153.95, 153.63, 153.08, 141.07, 139.09, 138.93, 134.42, 130.18, 124.72, 123.15, 120.31, 111.04, 69.36, 67.42, 54.57 ppm.

UV-vis (DMF) $\lambda_{max}$ (%): 672 (100), 606 (9), 341(11).

ESI-MS: m/z 375 [(M-2Cl)$^{2+}$]

The invention claimed is:

1. Process for preparing chlorides of phthalocyanine derivatives of formula (I)

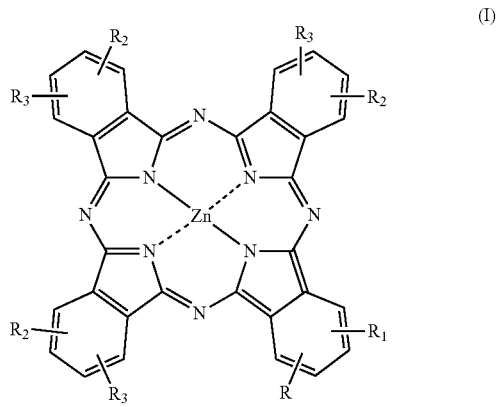

in which
R is selected from the group consisting of H, groups containing at least one quaternary ammonium substituent, a group suitable for binding by means of covalent bonds, and a bio-organic carrier selected from the group consisting of amino acids, polypeptides, proteins, antibodies, polysaccharides and aptamers, $R_1$, being the same as or different from R, is chosen from H and groups containing at least one quaternary ammonium substituent, $R_2$ and $R_3$, being the same or different, are selected from the group consisting of H, alkoxy or thioalkoxy groups having from 1 to 10 carbon atoms, and groups containing at least one quaternary ammonium substituent, with the proviso that:
a) at least one from R, $R_1$, $R_2$ and $R_3$ is a group containing at least one quaternary ammonium substituent and that, when R, $R_1$, $R_2$ and $R_3$ are groups containing at least one quaternary ammonium substituent, or R and $R_2$ are groups containing at least one quaternary ammonium substituent and $R_1$ and $R_3$ are H, said groups containing at least one quaternary ammonium substituent are the same;

b) when R and $R_1$ are both different from H, they are in positions 1,4 or 2,3, whereas when only one of R and $R_1$ is different from H, it is in position 1 or 2;

c) when $R_2$ and $R_3$ are both different from H they are in positions 8, 11, 15, 18, 22, 25 or 9, 10, 16, 17, 23, 24 whereas when only one of $R_2$ and $R_3$ is different from H, it is in positions 8(11), 15(18), 22(25) or in positions 9(10), 16(17), 23(24);

said process comprising the following steps:

i) reacting a phthalocyanine of formula (II) with a suitable alkylating agent to obtain the corresponding salt of the phthalocyanine of formula (I):

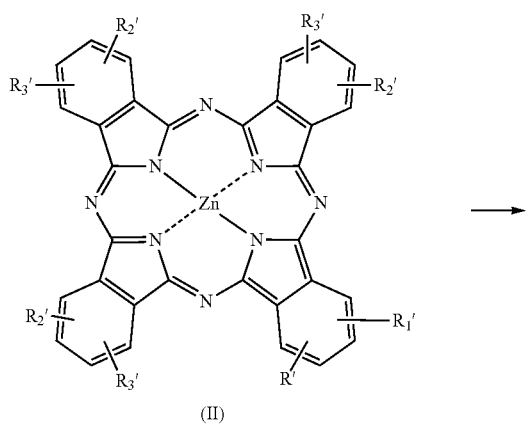

(II)

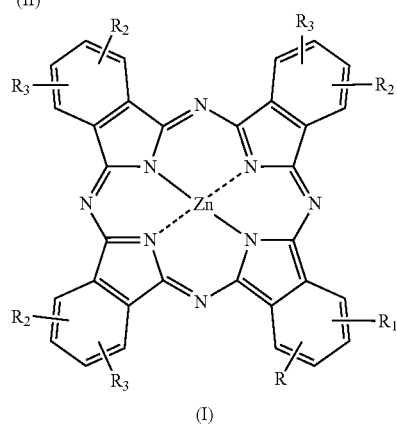

(I)

in which R, $R_1$, $R_2$ and $R_3$ are as defined above, while R', $R'_1$, $R'_2$, $R'_3$ are corresponding groups containing at least one amino substituent, corresponding respectively to R, $R_1$, $R_2$, and $R_3$ when R, $R_1$, $R_2$ and $R_3$ are groups containing at least one quaternary ammonium substituent, while being the same as R, $R_1$, $R_2$ and $R_3$ in all other cases, with the proviso that at least one of R', $R'_1$, $R'_2$ and $R'_3$ is a group containing at least one amino substituent and that the positions occupied by R', $R'_1$, $R'_2$, $R'_3$ are the same as specified above for R, $R_1$, $R_2$, $R_3$;

ii) treating the ammonium salt of the phthalocyanine of formula (I) coming from step i) with a suitable ion exchange resin to obtain the corresponding phthalocyanine of formula (I) in chloride form.

2. The process according to claim 1, wherein R=R'=$R_2$=$R_2'$=H, $R_1$=$R_3$=group containing at least one quaternary ammonium group and $R_1'$=$R_3'$=group containing at least one amino group corresponding to said quaternary ammonium.

3. The process according to claim 1, wherein R=$R_1$=$R_2$=$R_3$=group containing at least one quaternary ammonium group and R'=$R_1'$=$R_2'$=$R_3'$=group containing at least one amino group corresponding to said quaternary ammonium.

4. The process according to claim 1, wherein R=group containing at least one quaternary ammonium group, R'=group containing at least one amino group corresponding to said quaternary ammonium, $R_1$=$R_1'$=H or $R_1$=R and $R_1'$=R', and $R_2$=$R_2'$=$R_3$=$R_3'$=H.

5. The process according to claim 1, wherein R=R'=a group suitable for binding by means of covalent bonds, or a bio-organic carrier selected from the group consisting of amino acids, polypeptides, proteins, antibodies, polysaccharides and aptamers, $R_1$=$R_1'$=H, $R_2$=group containing at least one quaternary ammonium group, $R_2'$=group containing at least one amino group corresponding to said quaternary ammonium, $R_3$=$R_2$, H and $R_3'$=$R_2'$, H.

6. The process according to claim 1, wherein said group containing at least one quaternary ammonium substituent is a $(X)_p R_4$ group, where X is selected from the group consisting of O, —$CH_2$—, CO, S, SO, and —$NR_5$ where $R_5$ is chosen from H and C1-C15 alkyl; and $R_4$ is

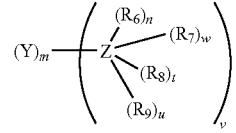

in which

Y is selected from the group consisting of C1-10 alkyl and phenyl, possibly substituted, or forms with the Z group, to which it is bound, a saturated or unsaturated heterocycle, possibly substituted, which may contain up to two heteroatoms selected from the group consisting of N, O and S;

Z is selected from the group consisting of N, —$CH_2$N and —$CONHCH_2CH_2N$;

$R_6$ and $R_7$, equal or different from one another, are selected from the group consisting of C1-15 alkyl and phenyl or form with the Z group, to which they are bound, a saturated or unsaturated heterocycle, possibly substituted, which may contain up to two heteroatoms selected from the group consisting of N, O and S;

$R_8$ and $R_9$, equal or different from one another, are selected from the group consisting of H and C1-15 alkyl;

m, n, p, w, t and u, independently from one another, are 0 or 1; and v is an integer between 1 and 3, with the proviso that only one from n, w, t and u is simultaneously 0.

7. The process according to claim 1, wherein said corresponding group containing at least one amino substituent is a $(X)_p R_4$ group as defined in claim 6, in which two of n, w, t and u are simultaneously 0.

8. The process according to claim 1, wherein said group containing at least one quaternary ammonium substituent is chosen from the following:

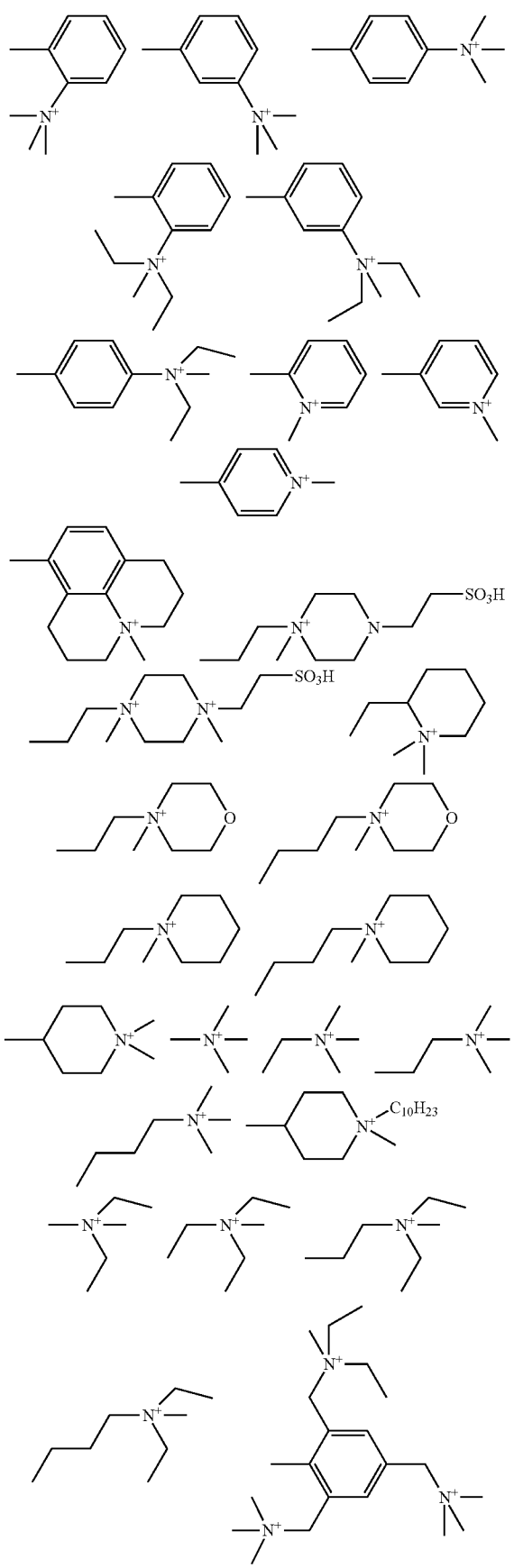
-continued
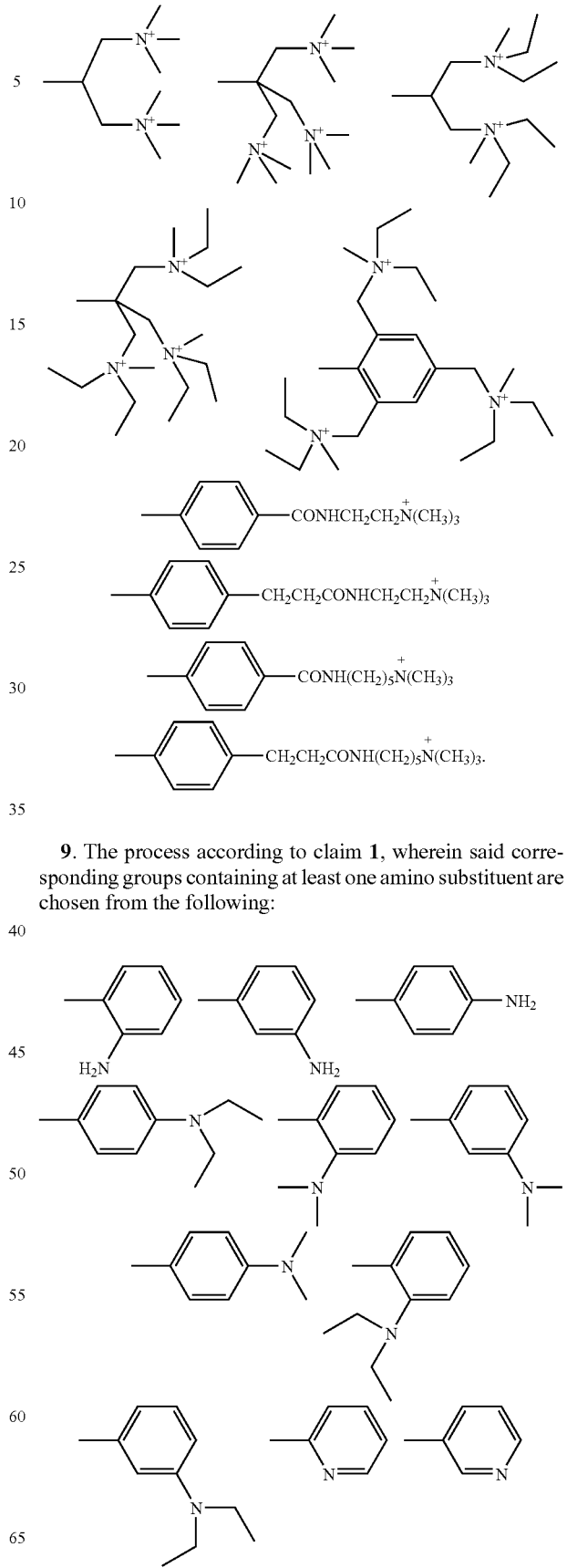
9. The process according to claim 1, wherein said corresponding groups containing at least one amino substituent are chosen from the following:

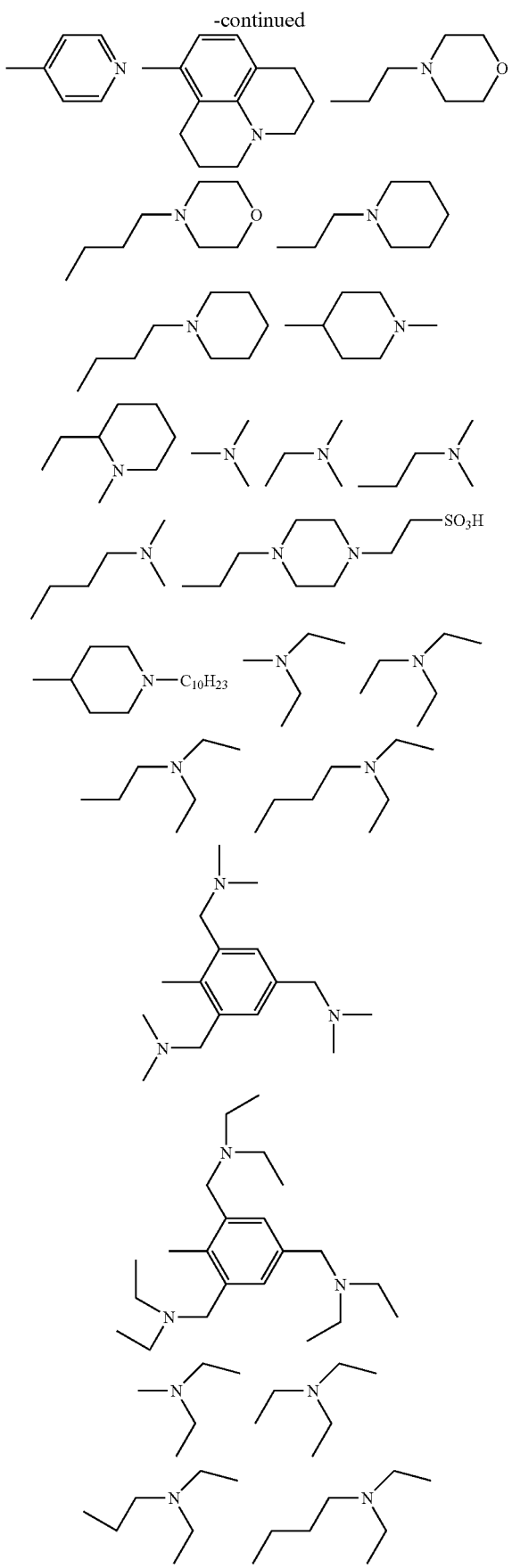
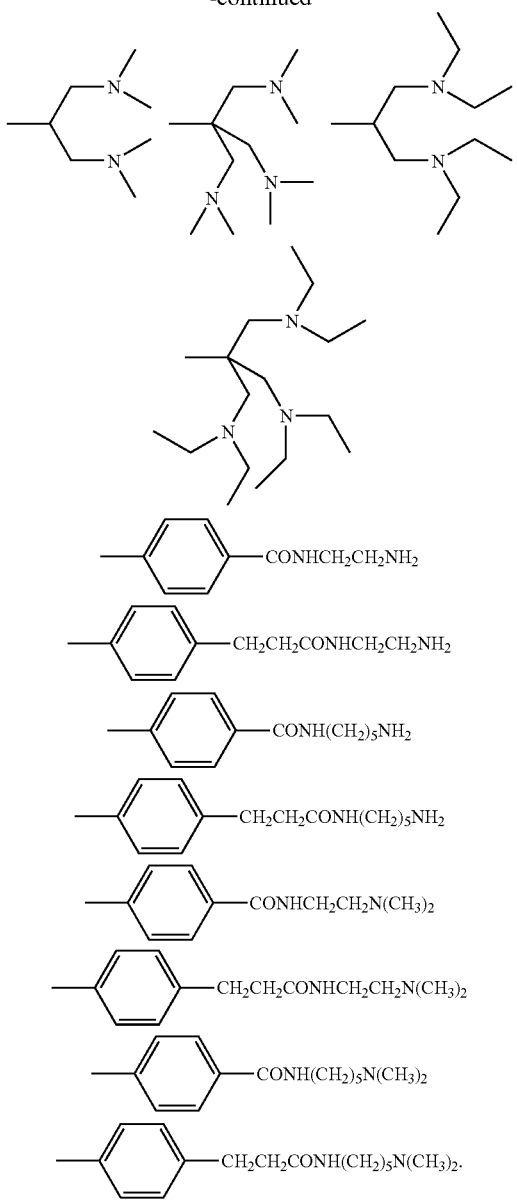
10. The process according to claim 8, wherein said group containing at least one quaternary ammonium substituent is chosen from the following:
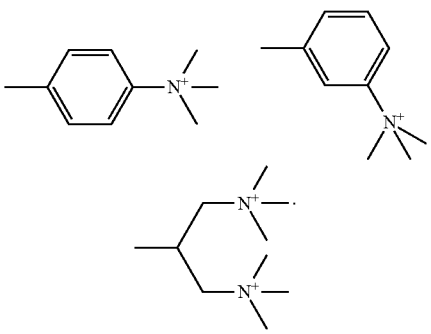

11. The process according to claim 9, wherein said corresponding groups containing at least one amino substituent are groups chosen from the following:

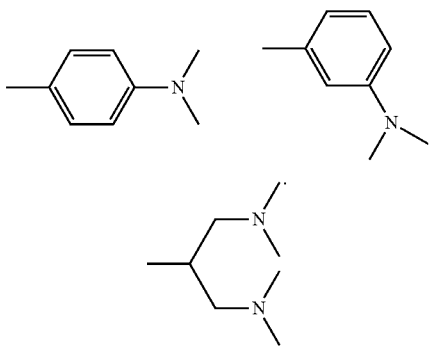

12. The process according to claim 6, wherein said saturated or unsaturated heterocycle is selected from the group consisting of morpholine, piperidine, pyridine, pyrimidine, piperazine, pyrrolidine, pyrroline, imidazole, aniline and julolidine.

13. The process according to claim 1, wherein said group suitable for binding by means of covalent bonds is selected from the group consisting of —COOH, —SH, —OH, —NH$_2$, —CO—CH$_2$—Br, —SO$_2$Cl, maleimide, hydrazide, phenol, imido, biotin, possibly bound to the phthalocyanine nucleus through a suitable spacer (X)$_p$—W, where X and p are defined as in claim 6 and W is chosen from C1-C10 alkyl, aryl, and C1-C5 arylalkyl.

14. The process according to claim 1, wherein said suitable alkylating agent in step i) is selected from the group consisting of alkyl bromide, iodide or sulfate, being preferably a C1-C5 linear alkyl iodide.

15. The process according to claim 14, wherein said suitable alkylating agent in step i) is methyl iodide.

16. The process according to claim 15, wherein said methyl iodide is utilised in a quantity comprised between 1 and 20 equivalents per amino group to be methylated, preferably in a quantity comprised between 5 and 11 equivalents.

17. The process according to claim 1, wherein said alkylating reaction in step i) is undertaken in a solvent chosen from dimethylformamide, dimethylsulfoxide and N-methylpyrrolidone, preferably in N-methylpyrrolidone.

18. The process according to claim 17, wherein the reaction product in step i) is precipitated from the solution in N-methylpyrrolidone with ethyl ether or isopropyl ether in a quantity of 4 to 8 volumes with respect to the volume of N-methylpyrrolidone, after having diluted the solution in N-methylpyrrolidone with methanol in a quantity of 1 to 2 volumes with respect to the volume of N-methylpyrrolidone.

19. The process according to claim 1, wherein said ion exchange resin in step ii) is chosen from among strong basic resins with quaternary ammonium functional groups.

20. The process according to claim 19, wherein said resin is a polystyrene based resin with a degree of cross-linking comprised between 4 and 10%.

21. The process according to claim 1, wherein said treatment of the salt in step ii) is undertaken by a chromatography process by using a solution of said salt of the phthalocyanine of formula (I), different from the chloride, and said ion exchange resin, and recovering the phthalocyanine of formula (I) in chloride form by evaporation, lyophilisation or precipitation.

22. The process according to claim 21, wherein said chromatography is undertaken by passing through the ion exchange resin a solution of the phthalocyanine salt of formula (I) in an alcoholic solvent, preferably methanol, or in a mixture of said alcoholic solvent with water or other solvents, in which the quantity of alcoholic solvent is preferably at least equal to 70%, and re-precipitating from the eluate the phthalocyanine of formula (I) in the chloride form by treating with a precipitating agent, preferably chosen from ethers.

23. The process according to claim 21, wherein said chromatography is undertaken by passing through the ion exchange resin a solution of the phthalocyanine salt of formula (I) in methanol, or in a mixture of methanol with a solvent of high solubilizing strength such as DMSO or DMF, then treating the eluate with ethyl ether to precipitate the phthalocyanine of formula (I) in chloride form.

24. The process according to claim 1, wherein said phthalocyanine of formula (II) is obtained by condensation of the substituted phthalonitriles of formula (III) and (IV)

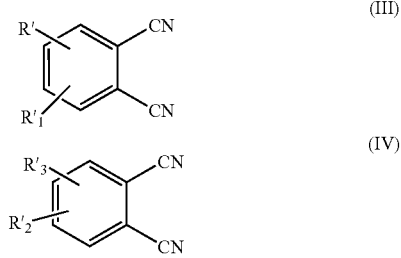

in which R', R'$_1$, R'$_2$ and R'$_3$ are defined as in claim 1, in the presence of a base and possibly an organic solvent, preferably a solvent miscible with water, more preferably DMF, and subsequent or simultaneous metal insertion by treating with a suitable Zinc(II) salt, preferably Zinc(II) acetate or Zinc(II) chloride.

25. The process according to claim 24, wherein when said phthalocyanine of formula (II) is non centrosymmetrical, said phthalonitriles of formula (III) and (IV) are used in a molar ratio comprised between 1:1 and 1:10, preferably in a molar ratio equal to 1:3.

26. The process according to claim 24, wherein said condensation reaction is carried out at a temperature comprised between 100 and 250° C., preferably comprised between 130 and 180° C.

27. The process according to claim 24, wherein said base is chosen from 1,5-diazabicyclo[5.4.0]non-5-ene (DBN), 1,8-diazabicyclo[5.4.0]undec-7-ene (DBU) and 2-dimethylamino-ethanol (DMAE).

28. The process according to claim 24, wherein said condensation reaction is carried out in the absence of solvent with DBU as the base, and at a temperature equal to 140° C.

29. The process according to claim 24, wherein the crude product of formula (II) obtained from the condensation is precipitated by treating the reaction mixture with water or mixtures of water and water miscible solvents, filtering or centrifuging the suspension then washing the recovered solid several times with water and/or water miscible solvents, preferably with alcohols.

30. The process according to claim 24, further comprising purification of the crude product of formula (II) obtained from condensation by means of column chromatography followed by re-precipitation from solvent, before undergoing step i).

31. The process according to claim 30, wherein said column chromatography is undertaken using silica gel or alumina as the stationary phase and a mixture of organic solvents as the mobile phase.

32. The process according to claim 31, wherein said mixture of organic solvents is composed of two or more solvents selected from the group consisting of THF, methanol, ethyl ether, n-hexane, DMF and chloride solvents, provided that said mixture always contains a quantity of chlorinated solvents or THF greater than 30%.

33. The process of claim 1, wherein said group suitable for binding by means of covalent bonds is selected from the group consisting of —COOH, —SH, —OH, —NH$_2$, —CO—CH$_2$—Br, —SO$_2$Cl, maleimide, hydrazide, phenol, imido, biotin, possibly bound to the phthalocyanine nucleus through a suitable spacer $(X)_p$—W, where X and p are defined as above and W is chosen from C1-C10 alkyl, aryl, and C1-C5 arylalkyl.

34. The process of claim 5, wherein said group suitable for binding by means of covalent bonds is selected from the group consisting of —COOH, —SH, —OH, —NH$_2$, —CO—CH$_2$—Br, —SO$_2$Cl, maleimide, hydrazide, phenol, imido, biotin, possibly bound to the phthalocyanine nucleus through a suitable spacer $(X)_p$—W, where X and p are defined as above and W is chosen from C1-C10 alkyl, aryl, and C1-C5 arylalkyl.

* * * * *

UNITED STATES PATENT AND TRADEMARK OFFICE
CERTIFICATE OF CORRECTION

PATENT NO. : 8,242,262 B2
APPLICATION NO. : 11/913540
DATED : August 14, 2012
INVENTOR(S) : Dei et al.

It is certified that error appears in the above-identified patent and that said Letters Patent is hereby corrected as shown below:

Col. 19, In Claim 8, please change

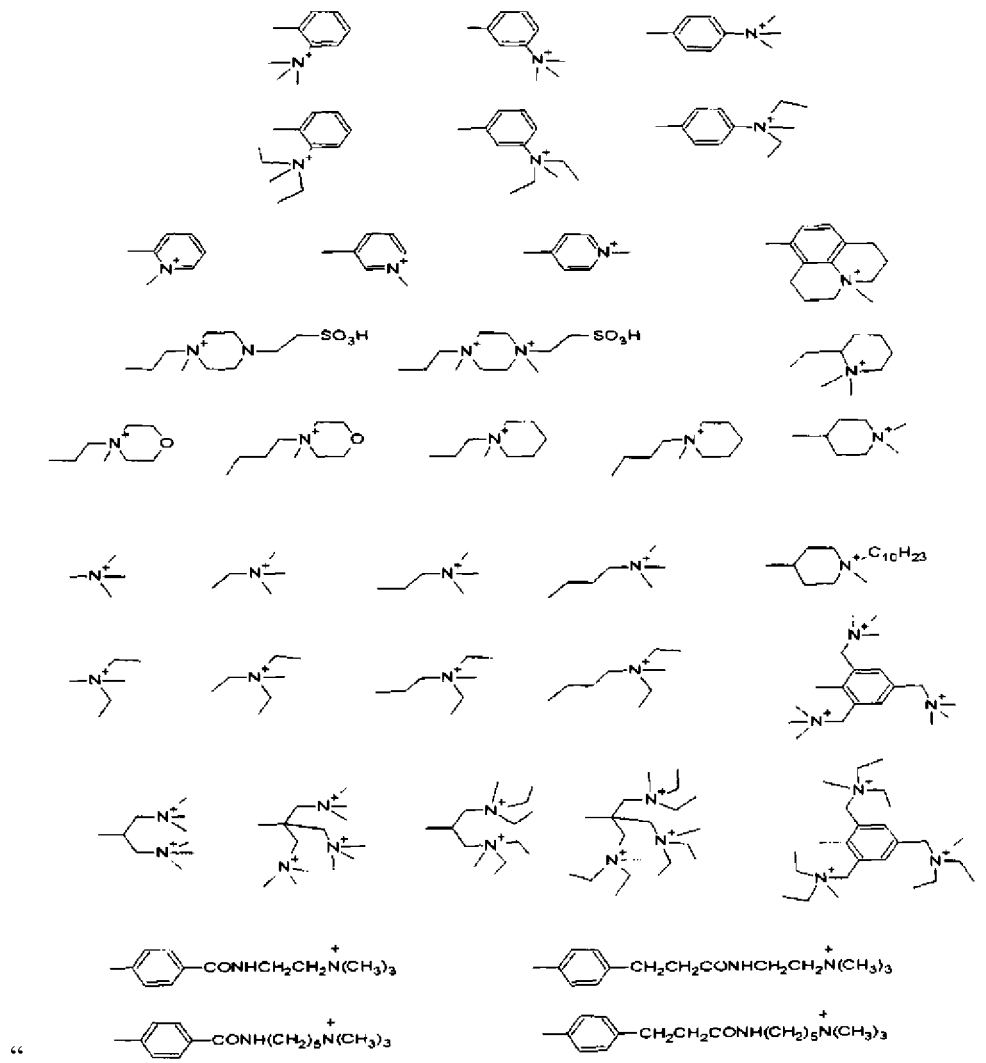

Signed and Sealed this
Nineteenth Day of March, 2013

Teresa Stanek Rea
*Acting Director of the United States Patent and Trademark Office* to:
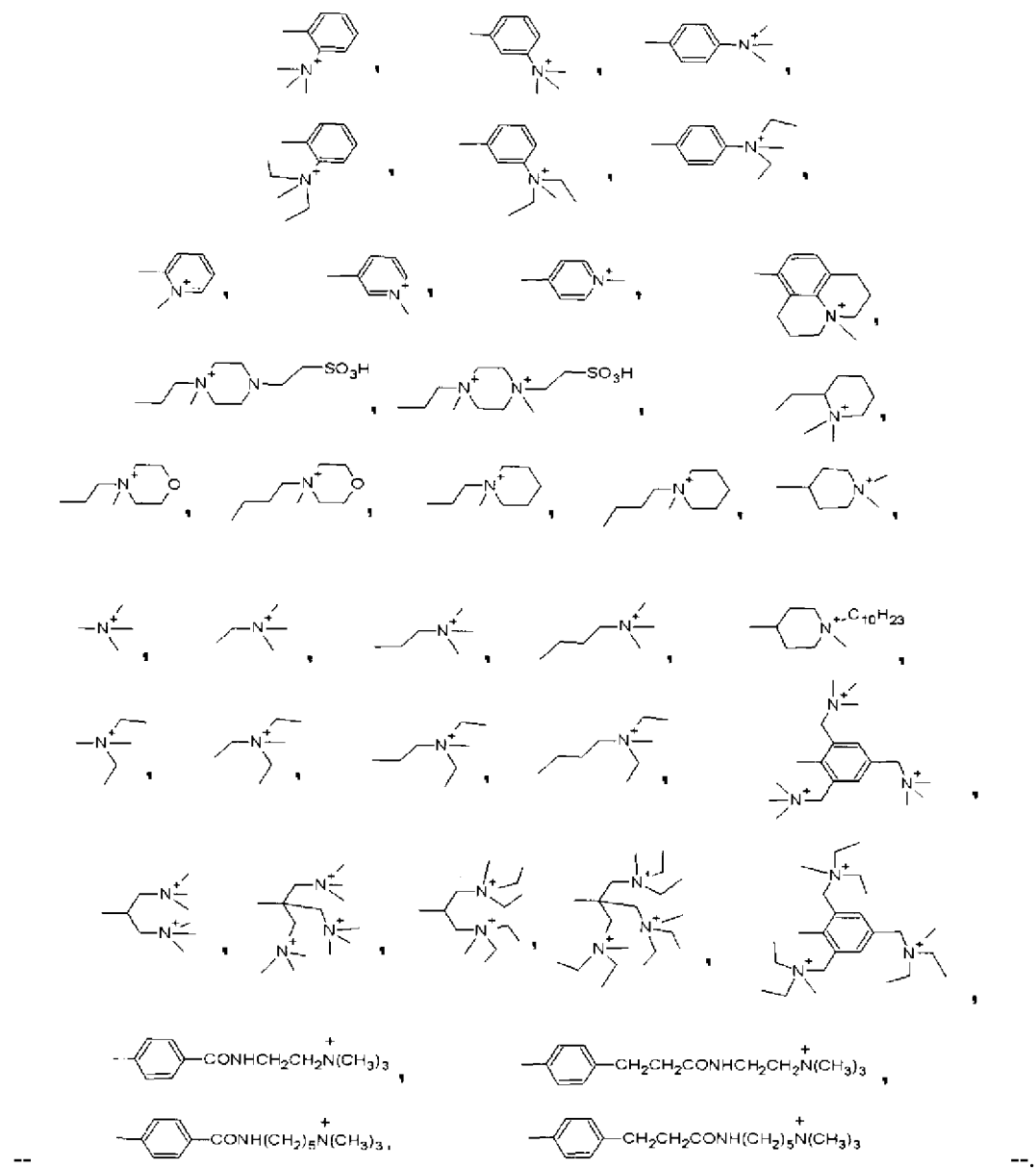

CERTIFICATE OF CORRECTION (continued)
U.S. Pat. No. 8,242,262 B2

Column 19 - 20, In Claim 9, please change

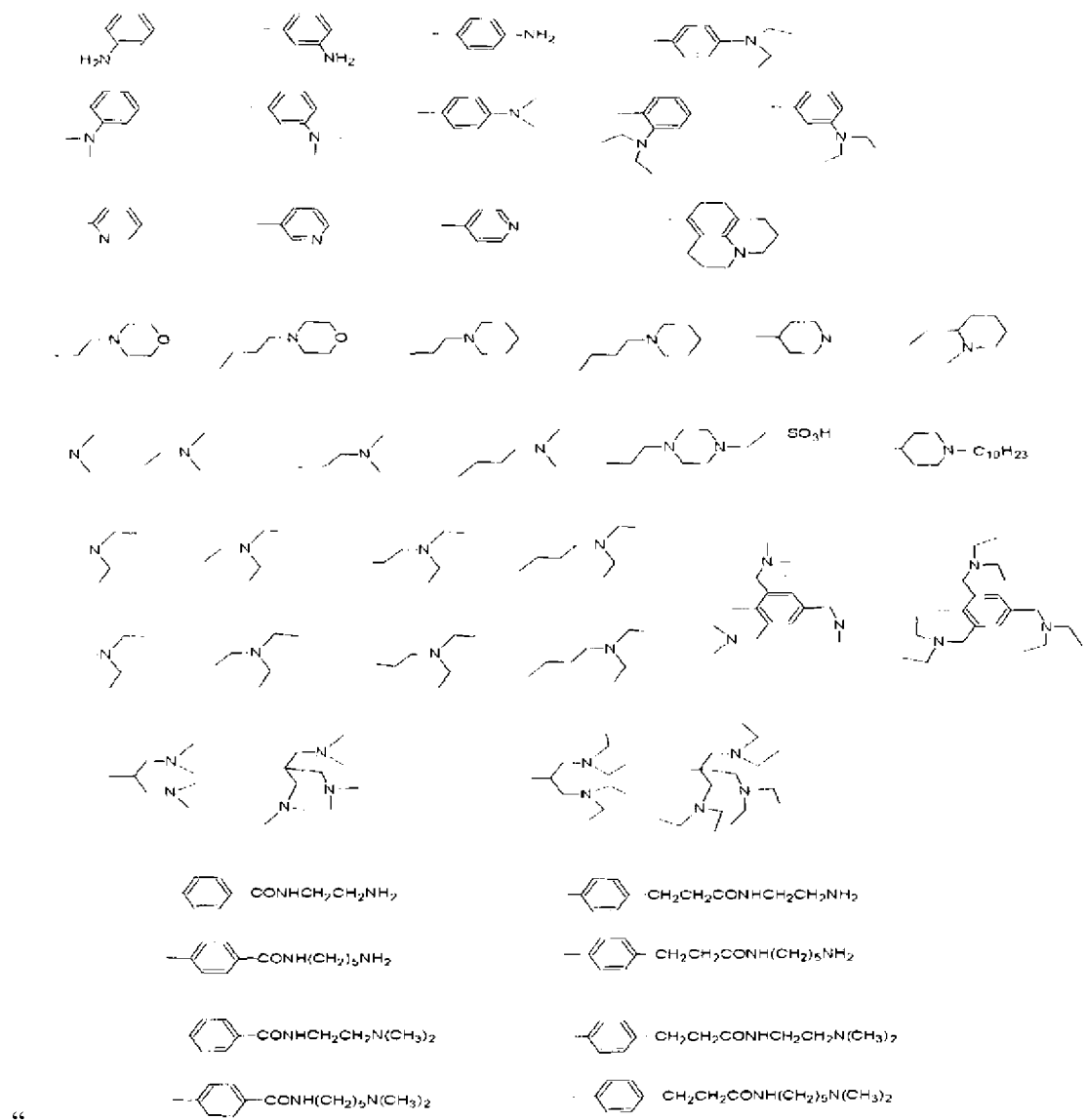

to:
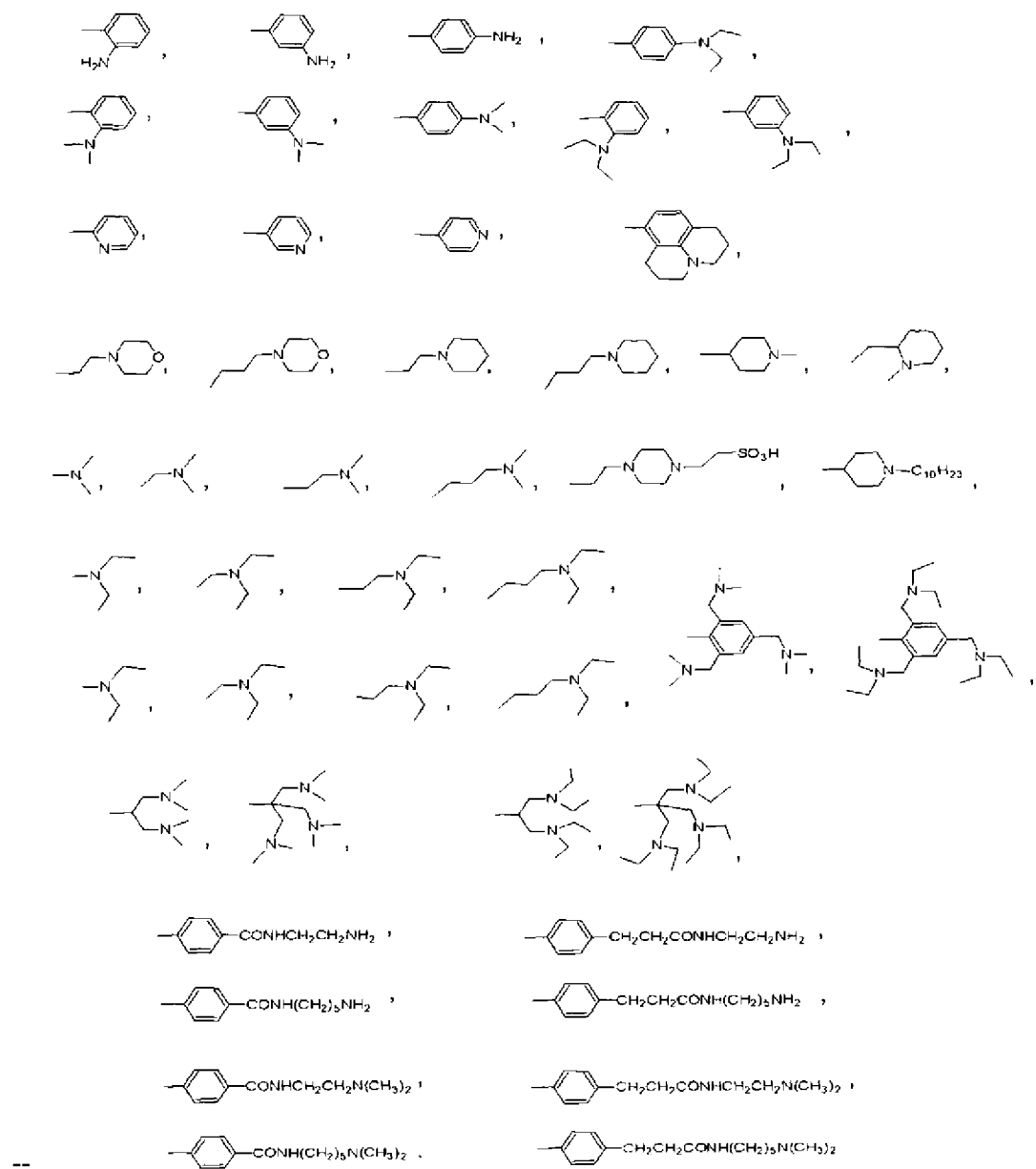
--                                                                                                              --.

CERTIFICATE OF CORRECTION (continued)
U.S. Pat. No. 8,242,262 B2

Column 22, In Claim 10, please change

"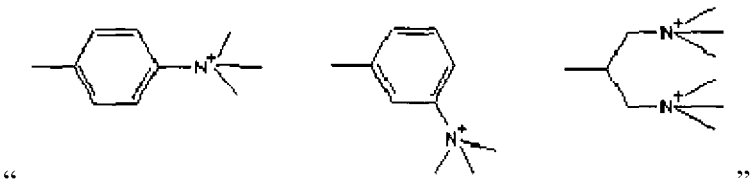"

to:

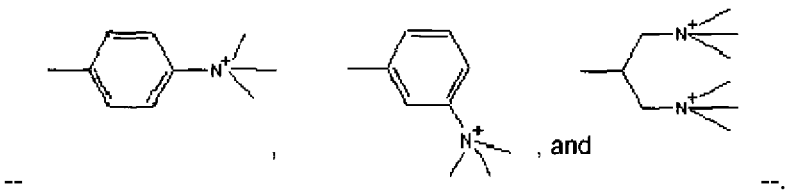

--.

Column 23, In Claim 11, please change

"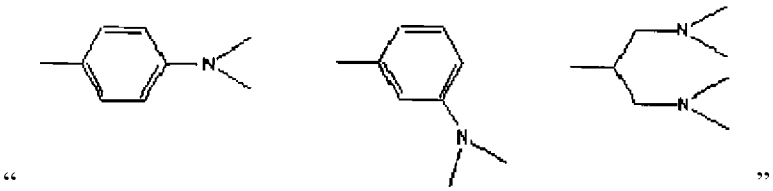"

to:

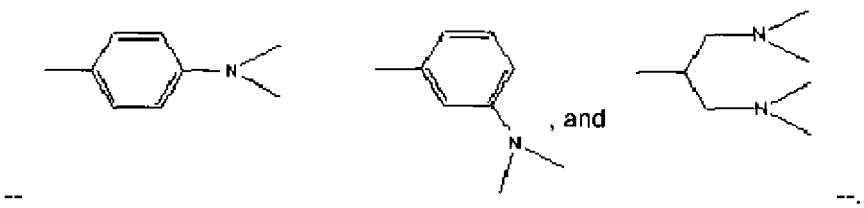

--.